(12) United States Patent
Pinsonneault et al.

(10) Patent No.: US 8,392,219 B1
(45) Date of Patent: Mar. 5, 2013

(54) SYSTEMS AND METHODS FOR STREAMLINED PATIENT ENROLLMENT FOR ONE OR MORE HEALTHCARE PROGRAMS

(75) Inventors: Roger Pinsonneault, Alpharetta, GA (US); Patrick Harris, Sr., Atlanta, GA (US)

(73) Assignee: McKesson Financial Holdings Limited (BM)

( * ) Notice: Subject to any disclaimer, the term of this patent is extended or adjusted under 35 U.S.C. 154(b) by 109 days.

(21) Appl. No.: 12/776,974

(22) Filed: May 10, 2010

(51) Int. Cl.
*A61B 5/00* (2006.01)

(52) U.S. Cl. .................. 705/3; 705/2; 715/733

(58) Field of Classification Search .......... 705/2, 3; 715/733
See application file for complete search history.

(56) References Cited

U.S. PATENT DOCUMENTS

| | | | |
|---|---|---|---|
| 5,628,530 A | 5/1997 | Thornton | |
| 5,970,472 A | 10/1999 | Allsop et al. | |
| 6,012,035 A | 1/2000 | Freeman et al. | |
| 6,045,501 A | 4/2000 | Elsayed et al. | |
| 6,055,507 A | 4/2000 | Cunningham | |
| 6,315,720 B1 | 11/2001 | Williams et al. | |
| 6,561,976 B2 | 5/2003 | Elsayed et al. | |
| 6,561,977 B2 | 5/2003 | Williams et al. | |
| 6,602,469 B1 | 8/2003 | Maus et al. | |
| 6,757,898 B1 | 6/2004 | Ilsen et al. | |
| 6,769,228 B1 | 8/2004 | Mahar | |
| 6,952,681 B2 | 10/2005 | McQuade et al. | |
| 6,994,249 B2 | 2/2006 | Peterka et al. | |
| 7,040,856 B2 | 5/2006 | Reich | |
| 7,086,133 B2 | 8/2006 | Reich | |
| 7,096,072 B2 | 8/2006 | Engleson et al. | |
| 7,103,419 B2 | 9/2006 | Engleson et al. | |
| 7,107,106 B2 | 9/2006 | Engleson et al. | |
| 7,117,041 B2 | 10/2006 | Engleson et al. | |
| 7,155,397 B2 | 12/2006 | Alexander et al. | |
| 7,171,277 B2 | 1/2007 | Engleson et al. | |

(Continued)

FOREIGN PATENT DOCUMENTS

| CA | 2482370 A1 | 3/2006 |
|---|---|---|
| WO | WO 9503569 A3 | 2/1995 |

(Continued)

OTHER PUBLICATIONS

Non-Final Office Action for U.S. Appl. No. 12/212,129 mailed Apr. 18, 2011.

(Continued)

*Primary Examiner* — Dilek B Cobanoglu
(74) *Attorney, Agent, or Firm* — Sutherland Asbill & Brennan LLP (57) ABSTRACT

Systems and methods are provided for supporting and validating patient enrollment in one or more healthcare programs. The systems and methods may include receiving a prescription claim request from a pharmacy computer, where the prescription claim request includes at least (i) a first product identifier identifying with a prescribed product for a patient, and (ii) patient information associated with the patient; determining, based at least in part upon the first identifier, that patient is subject to a requirement to enroll in one or more required healthcare programs prior to the prescription product being released to the patient; extracting enrollment information from the prescription claim request, the extracted enrollment information including at least a portion of the patient information from the prescription claim request; and automatically utilizing the extracted enrollment information to complete at least a portion of an enrollment process for the one or more required healthcare programs.

20 Claims, 5 Drawing Sheets

U.S. PATENT DOCUMENTS

| | | | |
|---|---|---|---|
| 7,175,081 | B2 | 2/2007 | Andreasson et al. |
| 7,469,213 | B1 | 12/2008 | Rao |
| 7,483,756 | B2 | 1/2009 | Engleson et al. |
| 7,668,730 | B2 | 2/2010 | Reardan et al. |
| 7,739,127 | B1 | 6/2010 | Hall |
| 7,765,106 | B2 | 7/2010 | Reardan et al. |
| 7,765,107 | B2 | 7/2010 | Reardan et al. |
| 7,813,938 | B2 | 10/2010 | Kusterbeck |
| 7,885,824 | B1 | 2/2011 | Koneru |
| 7,895,059 | B2 | 2/2011 | Reardan et al. |
| 7,976,508 | B2 | 7/2011 | Hoag |
| 8,036,911 | B2 | 10/2011 | Bellon et al. |
| 8,112,290 | B2 * | 2/2012 | Maurer et al. ............. 705/2 |
| 2002/0002495 | A1 | 1/2002 | Ullman |
| 2002/0087583 | A1 | 7/2002 | Morgan et al. |
| 2002/0111828 | A1 | 8/2002 | Bloder et al. |
| 2002/0111832 | A1 | 8/2002 | Judge |
| 2002/0198831 | A1 | 12/2002 | Patricelli et al. |
| 2003/0009367 | A1 | 1/2003 | Morrison |
| 2003/0050799 | A1 | 3/2003 | Jay et al. |
| 2003/0055683 | A1 | 3/2003 | Gibson et al. |
| 2003/0149625 | A1 | 8/2003 | Leonardi et al. |
| 2003/0154163 | A1 | 8/2003 | Phillips et al. |
| 2003/0229540 | A1 | 12/2003 | Algiene |
| 2004/0019794 | A1 | 1/2004 | Moradi et al. |
| 2004/0039599 | A1 | 2/2004 | Fralic |
| 2004/0073457 | A1 | 4/2004 | Kalies |
| 2004/0078234 | A1 | 4/2004 | Tallal, Jr. |
| 2004/0117323 | A1 | 6/2004 | Mindala |
| 2004/0148198 | A1 | 7/2004 | Kalies |
| 2004/0249745 | A1 | 12/2004 | Baaren |
| 2005/0015280 | A1 | 1/2005 | Gabel et al. |
| 2005/0060201 | A1 | 3/2005 | Connely, III et al. |
| 2005/0102169 | A1 | 5/2005 | Wilson |
| 2005/0154627 | A1 | 7/2005 | Zuzek et al. |
| 2005/0187793 | A1 | 8/2005 | Myles |
| 2005/0197862 | A1 | 9/2005 | Paterson et al. |
| 2005/0240473 | A1 | 10/2005 | Ayers, Jr. et al. |
| 2005/0288972 | A1 | 12/2005 | Marvin et al. |
| 2006/0020514 | A1 | 1/2006 | Yered |
| 2006/0026041 | A1 | 2/2006 | Ullman |
| 2006/0054682 | A1 | 3/2006 | de la Huerga |
| 2006/0149784 | A1 | 7/2006 | Tholl et al. |
| 2006/0184391 | A1 | 8/2006 | Barre et al. |
| 2006/0259363 | A1 | 11/2006 | Jhetam et al. |
| 2007/0005402 | A1 | 1/2007 | Kennedy et al. |
| 2007/0043586 | A1 | 2/2007 | Arellano |
| 2007/0050209 | A1 | 3/2007 | Yered |
| 2007/0088461 | A1 | 4/2007 | Haitin et al. |
| 2007/0136100 | A1 | 6/2007 | Daugherty et al. |
| 2007/0233525 | A1 | 10/2007 | Boyle |
| 2007/0233526 | A1 | 10/2007 | Hoffman et al. |
| 2007/0239493 | A1 | 10/2007 | Sweetland et al. |
| 2007/0260491 | A1 | 11/2007 | Palmer et al. |
| 2008/0201173 | A1 | 8/2008 | Takehara et al. |
| 2008/0306796 | A1 | 12/2008 | Zimmerman et al. |
| 2009/0094051 | A1 | 4/2009 | Ard et al. |
| 2009/0125326 | A1 | 5/2009 | Wasson et al. |
| 2009/0246265 | A1 | 10/2009 | Stinchcomb et al. |
| 2010/0057489 | A1 | 3/2010 | Howe et al. |
| 2010/0082458 | A1 | 4/2010 | Godlewski |
| 2010/0256984 | A1 * | 10/2010 | Gold et al. ............. 705/2 |
| 2010/0287002 | A1 | 11/2010 | Barre et al. |
| 2011/0010328 | A1 | 1/2011 | Patel et al. |
| 2011/0106556 | A1 | 5/2011 | Patel et al. |
| 2011/0119085 | A1 | 5/2011 | Reardan et al. |
| 2011/0145018 | A1 | 6/2011 | Fotsch et al. |
| 2011/0182807 | A1 | 7/2011 | Fuisz et al. |
| 2011/0184747 | A1 | 7/2011 | Bozic et al. |
| 2011/0184753 | A1 | 7/2011 | Tripoli |
| 2011/0184755 | A1 | 7/2011 | Yamaga et al. |
| 2011/0184756 | A1 | 7/2011 | Yamaga et al. |
| 2011/0209065 | A1 * | 8/2011 | Del Rio et al. ............. 715/733 |

FOREIGN PATENT DOCUMENTS

| | | |
|---|---|---|
| WO | WO 0039737 A1 | 7/2000 |
| WO | WO 2007025295 A2 | 3/2007 |

OTHER PUBLICATIONS

Sampson, R.J., Taking Control of Health Care Costs, Best's Review—Life Health Insurance Edition, Nov. 1983, pp. 64-66, vol. 84, Issue 7, USA.

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic; On-line Goes In-House, Chain Store Age Executive, Jan. 1987, pp. 128-132. vol. 63, Issue 1, USA.

Anonymous, TechRx Announces Successful Beta Deployment of T-Rex. PR Newswire. May 13, 2002.

Non-Final Office Action for U.S. Appl. No. 12/468,102 mailed May 27, 2011.

Final Office Action for U.S. Appl. No. 12/212,129 mailed Aug. 18, 2011.

Final Office Action for U.S. Appl. No. 12/468,102 mailed Nov. 16, 2011.

Non-Final Office Action for U.S. Appl. No. 12/212,129 mailed Nov. 30, 2011.

Non-Final Office Action for U.S. Appl. No. 12/552,825 mailed Dec. 2, 2011.

Federal Register—vol. 77, No. 39; Tuesday, Feb. 28, 2012; Notices (pp. 12059-12062).

Final Office Action for U.S. Appl. No. 12/212,129 mailed Mar. 28, 2012.

Final Office Action for U.S. Appl. No. 12/552,825 mailed May 1, 2012.

Notice of Allowance for U.S. Appl. No. 12/212,129 mailed Dec. 31, 2012.

Final Office Action for U.S. Appl. No. 12/468,102 mailed Jan. 14, 2013.

* cited by examiner

SYSTEMS AND METHODS FOR STREAMLINED PATIENT ENROLLMENT FOR ONE OR MORE HEALTHCARE PROGRAMS

FIELD OF THE INVENTION

Aspects of the invention relate generally to healthcare programs, and more specifically to streamlined patient enrollment for one or more healthcare programs.

BACKGROUND OF THE INVENTION

Risk Evaluation and Mitigation Strategies (REMS) for highly regulated products oftentimes require patients to be enrolled in one or more healthcare programs. Currently, many healthcare programs require a physician or other prescriber to enroll a patient when prescribing a highly regulated product. However, the enrollment process can be labor-intensive for a physician or other prescriber, and may thus, provide a disincentive for the physician or other prescriber to prescribe a highly regulated product.

Thus, there is an opportunity for systems and methods for streamlined patient enrollment for one or more healthcare programs.

SUMMARY OF THE INVENTION

Some or all of the above needs and/or problems may be addressed by certain embodiments of the invention. Embodiments of the invention may include systems and methods for streamlined patient enrollment for one or more healthcare programs. In one embodiment, there is a computer-implemented method. The method may include: receiving a prescription claim request from a pharmacy computer, where the prescription claim request includes at least (i) a first product identifier identifying with a prescribed product for a patient, and (ii) patient information associated with the patient; determining, based at least in part upon the first identifier, that patient is subject to a requirement to enroll in one or more required healthcare programs prior to the prescription product being released to the patient; extracting enrollment information from the prescription claim request, the extracted enrollment information including at least a portion of the patient information from the prescription claim request; and automatically utilizing the extracted enrollment information to complete at least a portion of an enrollment process for the one or more required healthcare programs. One or more of the prior steps may be performed by one or more computers associated with a service provider.

In accordance with another embodiment of the invention, there is a system. The system may include at least one memory operable to store computer-executable instructions, and at least one processor configured to access the at least one memory. The at least one processor may be further be configured to execute the computer-executable instructions to: receive a prescription claim request from a pharmacy computer, where the prescription claim request includes at least (i) a first product identifier identifying with a prescribed product for a patient, and (ii) patient information associated with the patient; determine, based at least in part upon the first identifier, that patient is subject to a requirement to enroll in one or more required healthcare programs prior to the prescription product being released to the patient; extract enrollment information from the prescription claim request, the extracted enrollment information including at least a portion of the patient information from the prescription claim request; and automatically utilize the extracted enrollment information to complete at least a portion of an enrollment process for the one or more required healthcare programs.

BRIEF DESCRIPTION OF THE DRAWINGS

Reference will now be made to the accompanying drawings, which are not necessarily drawn to scale, and wherein.

DETAILED DESCRIPTION

Example embodiments of invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Embodiments of the invention are directed towards supporting patient enrollments in conjunction with prescription claim transactions provided by a pharmacy computer to a service provider computer. According to an example embodiment of the invention, a patient that is the subject of a prescription claim transaction may be determined as not being enrolled or registered for one or more healthcare programs. As such, patient enrollment information can be extracted from the prescription claim transaction, as well as from an external source, to facilitate patient enrollment in one or more healthcare programs. The facilitated patient enrollment may complete only a portion of the enrollment process, or may alternatively, complete a full enrollment process. If any part of the enrollment process remains incomplete, then the service provider computer can provide a response to the pharmacy computer that requests completion of the enrollment process, for example, at an Internet website/portal supporting an enrollment process for one or more healthcare programs. The response delivered by the service provider computer to the pharmacy computer can be a rejection response, according to an example embodiment of the invention.

The enrollment in one or more healthcare programs may be mandated by in accordance with a REMS for a prescribed product. The one or more healthcare programs may include Medication Therapy Management (MTM) or Disease/Condition Management counseling or services, Step Therapy, healthcare programs required for prior authorizations, clinical trials, or any number of other services. For example, the MTM counseling or services may include a pharmacist, pharmacy employee, or other healthcare provider obtaining healthcare information from a patient, and counseling the patient on the benefits and/or risks associated with utilization of the product. Example MTM counseling or services provided by the pharmacist, pharmacy employee, or other healthcare provider can include, but is not limited to, one or more of the following:

Performing a comprehensive medication review to identify, resolve and prevent medication-related problems, including adverse drug events with the prescribed product to be utilized;

Providing verbal or printed education and training designed to enhance patient understanding and appropriate use of the prescribed product, as well as to enhance patient understanding of benefits and risks of the prescribed product;

Obtaining necessary assessments of the patient's health status;

Formulating a product treatment plan;

Providing an updated Personal Medication Record (PMR) and Medication Action Plan (MAP) to each patient following each consultation;

Providing information, support services, and resources designed to enhance patient adherence for utilization of the prescribed product;

Documenting the care delivered and communication of essential information to the patient's primary care providers; and/or Referring the patient to an appropriate health care provider if necessary.

The term "product," and its pluralized form, as used herein, is intended to refer to any good, including a drug or other substance.

System Overview

Figure 1:
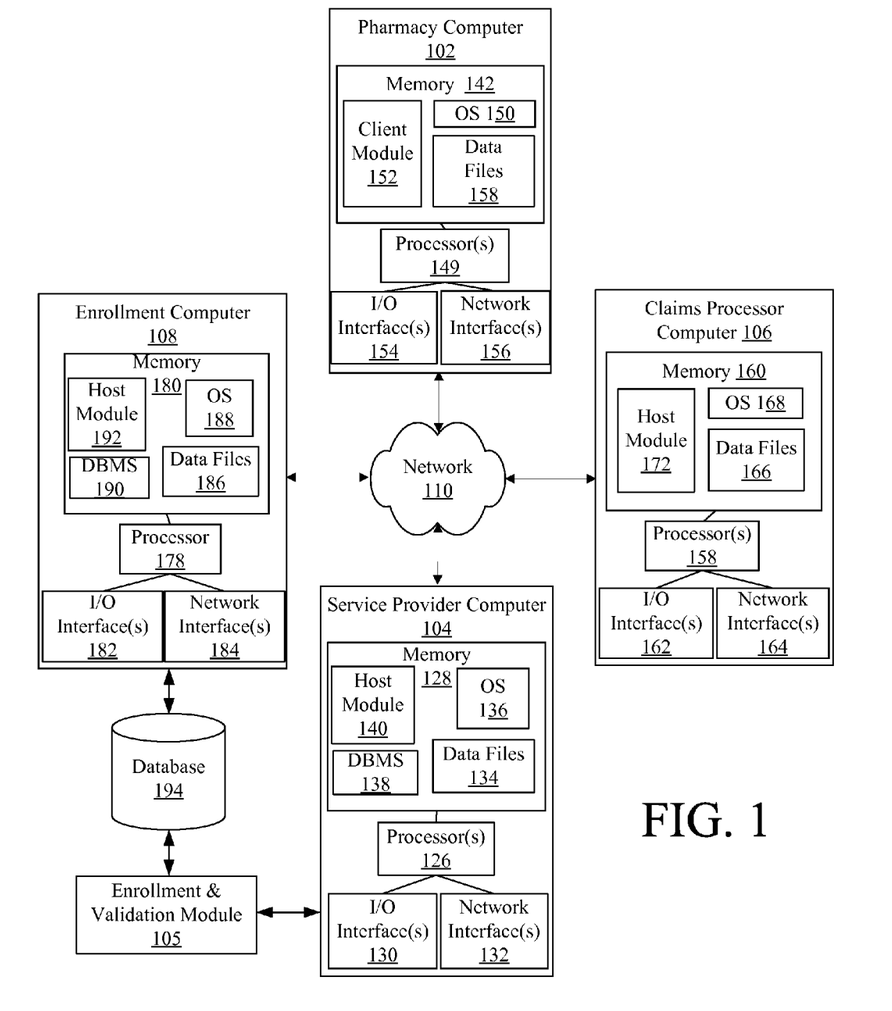
FIG. 1 illustrates an example healthcare system for supporting and validating patient enrollments for one or more healthcare programs for one or more products, according to an example embodiment of the invention.

FIG. 1 illustrates an example healthcare system 100 for supporting and a validating patient enrollments for one or more healthcare programs for one or more products, according to an example embodiment of the invention. As shown in FIG. 1, the system 100 may include a pharmacy computer 102, a service provider computer 104, a claims processor computer 106, and/or an enrollment computer 108, which are each configured for accessing and reading associated computer-readable media having stored thereon data and/or computer-executable instructions for implementing the various methods described herein. Generally, network devices and systems, including the one or more pharmacy computers 102, service provider computers 104, claims processor computers 106, and enrollment computers 108 have hardware and/or software for transmitting and receiving data and/or computer-executable instructions over a communications link and at least one memory for storing data and/or computer-executable instructions. These network devices and systems may also include a processor for processing data and executing computer-executable instructions, as well as other internal and peripheral components that are well known in the art. As used herein, the term "computer-readable medium" may describe any form of computer memory or memory device.

As shown in FIG. 1, the pharmacy computer 102, service provider computer 104, claims processor computer 106, and enrollment computer 108 may be in communication with each other via network 110, which as described below can include one or more separate or shared private and/or public networks, including the Internet. Each of these components—the pharmacy computer 102, the service provider computer 104, the claims processor computer 106, the enrollment computer 108, and the network 110—will now be discussed in further detail.

First, the pharmacy computer 102 may be any processor-driven device, such as a server computer, a mainframe computer, one or more networked computers, a desktop computer, a personal computer, a laptop computer, a mobile computer, a handheld portable computer, a digital assistant, a personal digital assistant, a digital tablet, an Internet appliance, or any other processor-based device. In addition to having processor(s) 149, the pharmacy computer 102 may further include a memory 142, input/output ("I/O") interface(s) 154, and network interface(s) 156. The memory 142 may store data files 158 and various program modules, such as an operating system ("OS") 150 and a client module 152. The memory 142 may be any computer-readable medium, coupled to the processor(s) 149, such as RAM, ROM, and/or a removable storage device for storing data files 158 and a database management system ("DBMS") to facilitate management of data files 158 and other data stored in the memory 142 and/or stored in separate databases. The OS 150 may be, but is not limited to, Microsoft Windows®, Apple OSX™, Linux, Unix, or a mainframe operating system. The client module 152 may be an Internet browser or other software, including a dedicated program, for interacting with the service provider computer 104 and/or enrollment computer 108. For example, a user such as a pharmacist, or other pharmacy employee, may utilize the client module 152 in preparing and providing a healthcare transaction request such as prescription claim request to the service provider computer 104. The pharmacy computer 102 may also utilize the client module 152 to retrieve or otherwise receive data from the service provider computer 104.

Second, the service provider computer 104 may include, but is not limited to, any processor-driven device that is configured for receiving, processing, and fulfilling requests from the pharmacy computer 102 and/or claims processor computer 106 relating to prescription, pharmacy, benefits, and/or other healthcare transactions or other activities. The service provider computer 104 may include, but is not limited to, a server computer, a mainframe computer, one or more networked computers, or any other processor-based device. According to an example embodiment of the invention, the service provider computer 104 may comprise, but is not limited to, one or more "switches" or "switch providers" performing routing and processing (e.g., pre- and post-routing editing) of prescription claim transactions between or among pharmacies, payors/claims processors, and/or other service providers.

The service provider computer 104 may include processor(s) 126, a memory 128, input/output ("I/O") interface(s) 130, and network interface(s) 132. The memory 128 may be any computer-readable medium, coupled to the processor(s) 126, such as RAM, ROM, and/or a removable storage device for storing data files 134 and a database management system ("DBMS") 138 to facilitate management of data files 134 and other data stored in the memory 128 and/or stored in one or more databases 182. The memory 128 may store data files 134 and various program modules, such as an operating system ("OS") 136, a database management system ("DBMS") 138, and the host module 140. The OS 136 may be, but is not limited to, Microsoft Windows®, Apple OSX™, Linux, Unix, or a mainframe operating system. The data files 134 may also store routing tables for determining the destination of communications received from the pharmacy computer 102 or the claims processor computer 106. The host module 140 may receive, process, and respond to requests from the client module 152 of the pharmacy computer 102, and may further receive, process, and respond to requests from the host module 172 of the claims processor computer 106 or the host module 192 of the enrollment computer 108.

An enrollment & validation module 105 may also be operative with the service provider computer 104. The enrollment & validation module 105 may include computer-executable instructions for supporting an enrollment of a patient in one or more healthcare programs or for validating that a patient has enrolled in one or more healthcare programs for one or more products. Enrollment or registration information used for the validation by the enrollment & validation module 105 may be accessible from database 194. The enrollment & validation module 105 may also store records relating to validations (e.g., date/time, approved, rejected) of prescription claims or other healthcare transactions in database 194. The enrollment & validation module 105 may be implemented as computer-implemented instructions of the memory 128 of the service provider computer 104. Alternatively, the enrollment & validation module 105 may also be implemented as computer-implemented instructions of a memory of separate processor-based system, according to an example embodiment of the invention.

The claims processor computer 106 may associated with an insurance company, a pharmacy benefits manager (PBM), a government payor, a discount processor, or the like, according to an example embodiment of the invention. The claims processor computer 106 may be any processor-driven device, such as, but not limited to, a server computer, a mainframe computer, one or more networked computers, a desktop computer, a personal computer, a laptop computer, a mobile computer, a handheld portable computer, a digital assistant, a personal digital assistant, a digital tablet, an Internet appliance, or any other processor-based device. The claims processor computer 106 may include processor(s) 158, a memory 160, input/output ("I/O") interface(s) 162, and network interface(s) 164. The memory 160 may be any computer-readable medium, coupled to the processor 158, such as RAM, ROM, and/or a removable storage device for storing data files 166 and a database management system ("DBMS") to facilitate management of data files 166 and other data stored in the memory 160 and/or stored in separate databases. The memory 160 may store data files 166 and various program modules, such as an operating system ("OS") 168, a database management system ("DBMS"), and a host module 172. The OS 168 may be, but is not limited to, Microsoft Windows®, Apple OSX™, Linux, Unix, or a mainframe operating system. The host module 172 may receive, process, and respond to requests from the client module 152 of the pharmacy computer 102, and may further receive, process, and respond to requests from the host module 140 of the service provider computer 104. According to an example embodiment of the invention, the claims processor computer 106 may be associated with coverage or benefits determination by an insurance company, a pharmacy benefits manger (PBM), a discount program, a government payor, or another third-party payor. According to an alternative example embodiment of the invention, a claims processor computer 106 may also be implemented as part of a service provider computer 104 or may otherwise be affiliated with the service provider computer 104.

Lastly, the enrollment computer 108 may include any processor-driven device that is configured for supporting enrollments of one or more patients in one or more healthcare programs associated with one or more products. If necessary or desired, a pharmacist or other individual/entity (e.g., physician/prescriber, pharmacy, patient, etc.) can complete an enrollment process for one or more healthcare programs with the enrollment computer 108 via a call center, interactive voice response (IVR) system, or Internet website or portal. The enrollment computer 108 may include a processor 178, a memory 180, input/output ("I/O") interface(s) 182, and a network interface 184. The memory 180 may store data files 186 and various program modules, such as an operating system ("OS") 188, a database management system ("DBMS") 190, and a host module 192. DBMS 190 may facilitate the management of data files 186 and other data stored in the memory 180 and/or stored in separate databases, including database 194. The host module 192 may receive, process, and respond to requests relating to enrollment or registration by a patient for one or more healthcare programs associated one or more products, according to an example embodiment of the invention. Information associated with an enrollment, either by the enrollment computer, service provider computer, and/or enrollment & validation module 105, may be stored in a database 194. As an example, the database 194 may include, but is not limited to, a REMS database or registry for storing enrollment information for patients for one or more healthcare programs.

The network 110 may include any telecommunication and/or data network, whether public, private, or a combination thereof, including a local area network, a wide area network, an intranet, an internet, the Internet, intermediate hand-held data transfer devices, a publicly switched telephone network (PSTN), and/or any combination thereof and may be wired and/or wireless. The network 110 may also allow for real-time, off-line, and/or batch transactions to be transmitted between or among the pharmacy computer 102, the service provider computer 104, the claims processor computer 106, and/or the enrollment computer 108. Due to network connectivity, various methodologies as described herein may be practiced in the context of distributed computing environments.

Those of ordinary skill in the art will appreciate that the system 100 shown in and described with respect to FIG. 1 is provided by way of example only. Numerous other operating environments, system architectures, and device configurations are possible. Accordingly, embodiments of the invention should not be construed as being limited to any particular operating environment, system architecture, or device configuration.

For example, it will be appreciated that in an alternative embodiment of FIG. 1, the operations of the enrollment computer 108 may be implemented as part of the service provider computer 104, perhaps as a module of the memory 128 of the service provider computer 104. Where the enrollment computer 108 is implemented as part of the service provider computer 104, the communications between the enrollment computer 108 and the service provider computer 104 may be accomplished via an internal or intra-network delivery. On the other hand, where the enrollment computer 108 is distinct from the service provider computer 104, the communications between the enrollment computer 108 and the service provider computer 104 may be accomplished via an external or inter-network delivery.

It will also be appreciated that while database 194 is illustrated as being shared between the enrollment & validation module 105 and the enrollment computer 108, the database 194 may be respective separate databases for each of the enrollment & validation module 105 and the enrollment computer 108. Information may be transferred from one database to another on a periodic basis, an as-needed basis, or an as-requested basis, according to an example embodiment of the invention.

Operational Overview

Figure 2A:
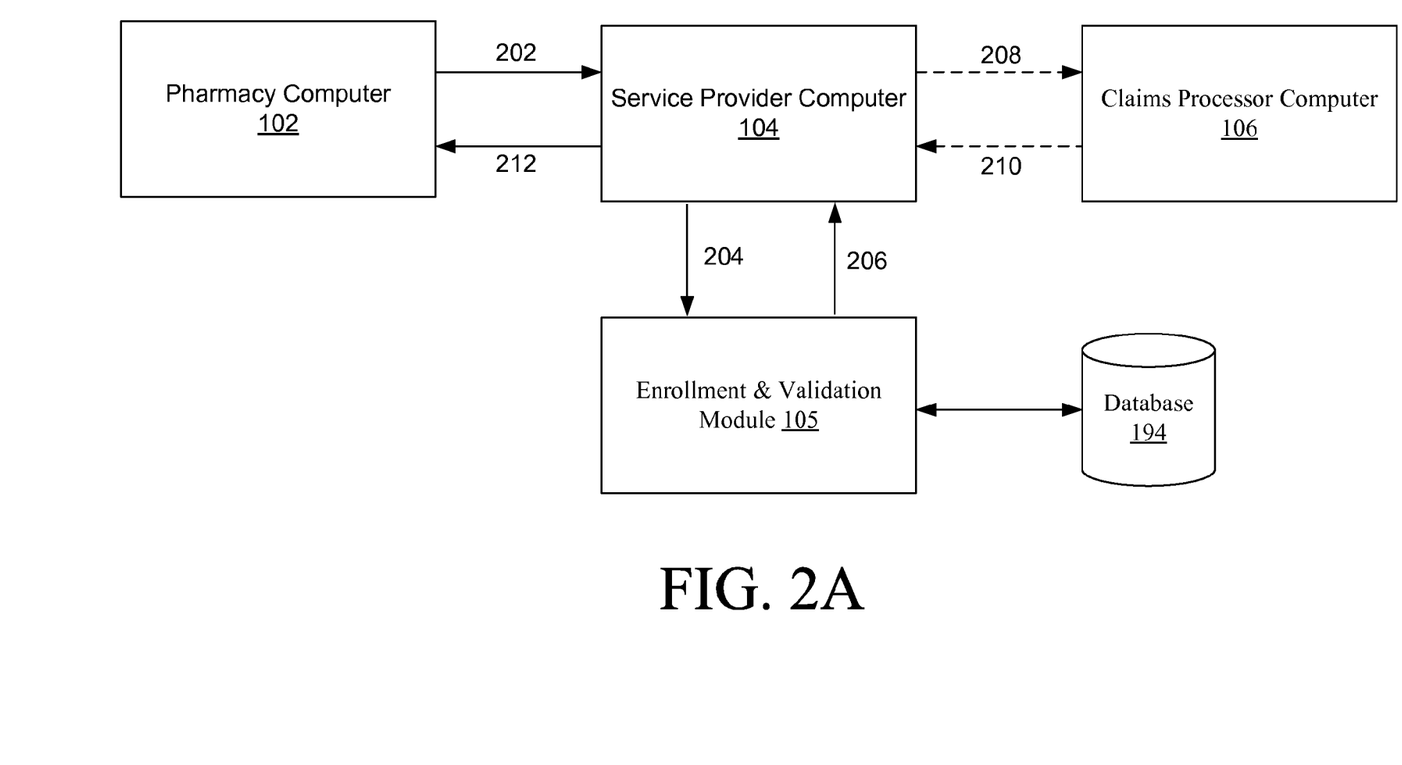
FIG. 2A illustrates an example block diagram for processing and validating patient enrollments for one or more healthcare programs, according to an example embodiment of the invention.

FIG. 2A illustrates an example block diagram for processing and validating patient enrollments for one or more healthcare programs, according to an example embodiment of the invention. The operation of the block diagram of FIG. 2A will be discussed in conjunction with the flow diagram of FIG. 3.

Figure 3:
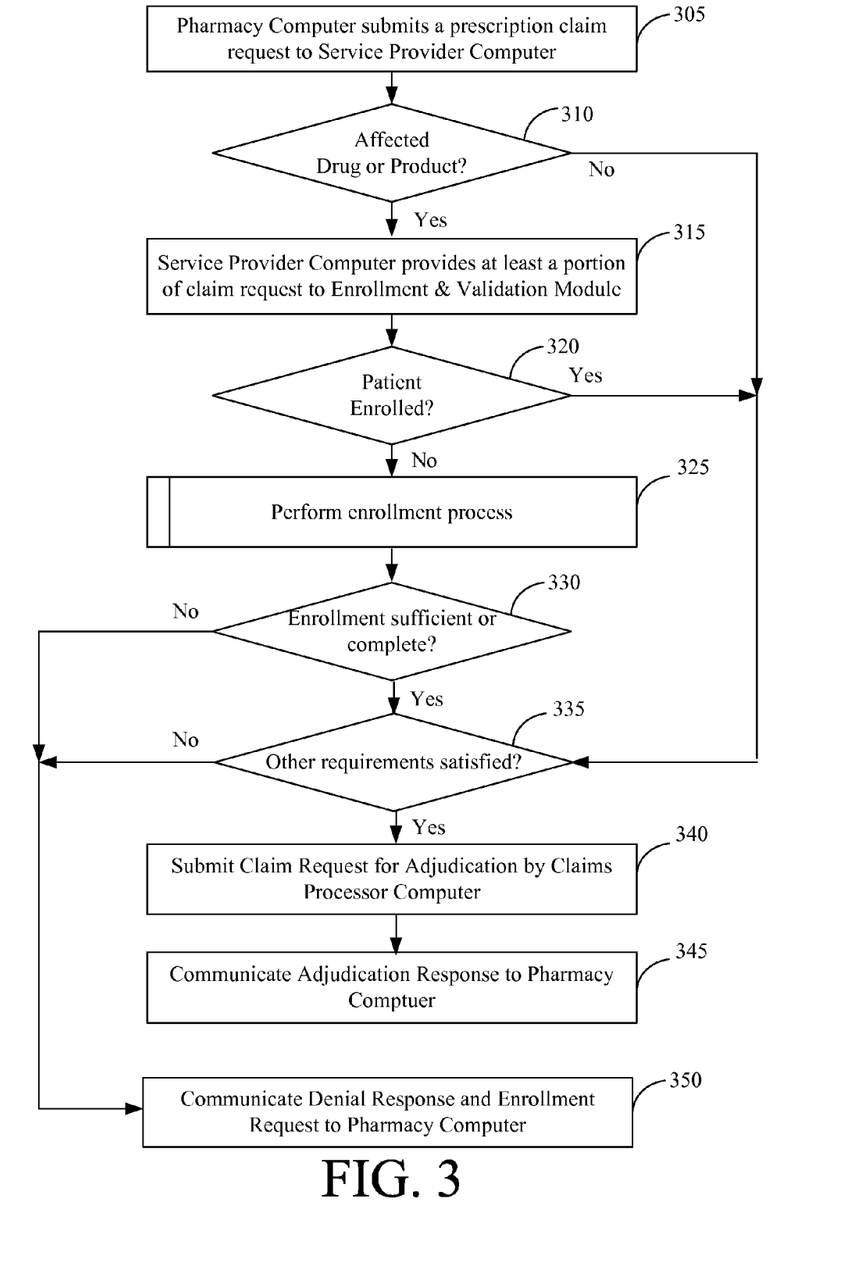
FIG. 3 illustrates an example flow diagram for processing and validating patient enrollments for one or more healthcare programs, according to an example embodiment of the invention.

Referring now to FIGS. 2A and 3, at block 305, a pharmacy may receive a prescription order for a product for a patient. The prescription order may be received in-person or electronically as desired in various embodiments of the invention. For example, a patient may present a paper prescription for a product at a pharmacy. As another example, an electronic prescription order (e.g., an E-SCRIPT) may be received by a pharmacy computer 102 as an electronic prescription order from a physician/prescriber/hospital/clinic computer. Still referring to block 305, a pharmacy computer 102 (e.g., a pharmacy computer) may generate a prescription claim request 202 based upon the received prescription order. The generated prescription claim request 202 may be communicated by the pharmacy computer 102 to the service provider computer 104. Thus, the service provider computer 104 may receive the prescription claim request 202. According to an example embodiment of the invention, the prescription claim request 202 may be in accordance with a version of a National Council for Prescription Drug Programs (NCPDP) Telecommunications Standard, although other standards may be utilized as well.

The prescription claim request 202 may include a BIN Number and/or a combination of a BIN Number and Processor Control Number (PCN) for identifying a particular claims processor computer or payer, such as the claims processor computer 106, as a destination for the prescription claim request 202. In addition, the prescription claim request 202 may also include information relating to the patient, payor, prescriber, healthcare provider, and/or the prescribed or administered drug or product. As an example, the prescription claim request 202 received by the service provider computer 104 may include one or more of the following information:

Payor ID/Routing Information
BIN Number and/or Processor Control Number (PCN) that designates a destination of the healthcare claim transaction
Patient Information
Name
  Patient First Name
  Patient Last Name
Date of Birth of Patient
Age of Patient
Gender
Patient Address (e.g., Street Address, Zip Code, etc.)
Patient Contact Information (e.g., Patient Telephone Number, email address, etc.)
Patient ID or other identifier
Insurance/Coverage Information
Cardholder Name (e.g., Cardholder First Name, Cardholder Last Name)
Cardholder ID and/or other identifier (e.g., person code)
Group ID and/or Group Information
State Payor Information
Provider Information
Prescriber Information
Primary Care Provider ID or other identifier (e.g., NPI code)
Primary Care Provider Name (e.g., Last Name, First Name)
Prescriber ID or other identifier (e.g., NPI code, DEA number)
Prescriber Name (e.g., Last Name, First Name)
Prescriber Contact Information (e.g., Telephone Number)
Pharmacy or other Healthcare Provider Information (e.g., store name, chain identifier, etc.)
Pharmacy or other Healthcare Provider ID (e.g., National Provider Identifier (NPI) code)
Claim Information
Drug or product information (e.g., National Drug Code (NDC))
Associated Prescription/Service Reference Number
Associated Prescription/Service Date
Date Prescription Written
Quantity Dispensed
Days Supply
Other Coverage Code
Diagnosis/Condition
Pricing information for the drug or product (e.g., network price, Usual & Customary price)
One or more Drug Utilization (DUR) Codes
Dispense as Written (DAW)/Product Selection Code
Date of Service.

It will be appreciated that while some example information has been illustrated for the example prescription claim request 202, alternate or additional information may also be included without departing from example embodiments of the invention.

At block 310, the service provider computer 104 may analyze the drug or product identified in the prescription claim request 202. In an example embodiment, block 310 may determine whether the prescription claim request 202 should be processed or validated by the enrollment & validation module 105 based upon the identified drug or product. For example, block 310 may include determining whether the identified drug or product in the prescription claim request 202 is a product that may be subject to one or more requirements, perhaps in accordance with a REMS, such as a requirement that a patient be enrolled in one or more healthcare programs prior to receiving the drug or product. In an example embodiment, at block 310, the service provider computer 104 may compare the identifier for the drug or product (e.g., National Drug Code (NDC)) from the request 202 with a list of identifiers for drugs or products that require processing or validation by the enrollment & validation module 105.

If block 310 determines that prescription claim request 202 does not require processing or validation by the enrollment & validation module 105, then processing may proceed to block 335, as described herein. On the other hand, if block 310 determines that the prescription claim request 202 does require processing or validation by the enrollment & validation module 105, then processing may proceed to block 315. At block 315, the service provider computer 104 may provide some or all of the information in the prescription claim request 202 as part of a request 204 to the enrollment & validation module 105 for processing or validation. Following block 315, processing may proceed to block 320, where the enrollment & validation module 105 may validate patient enrollment in one or more healthcare programs by the patient identified by the prescription claim request 202.

At block 320, the enrollment & validation module 105 may first determine, perhaps based upon stored requirements in database 194, which healthcare programs the patient is required to be enrolled or registered for. In an example embodiment of the invention, the one or more healthcare programs that a patient is required to be enrolled or registered for may be specified by REMS rules for that particular product. According to an example embodiment, block 320 may include validating that the patient identified in the claim request 202 (e.g., by Cardholder ID, First Name/Last Name/DOB, etc.) is likewise identified in the database 194 (e.g., in one or more matching records in a patient database or registry) as being enrolled for one or more required healthcare programs for the prescribed product identified by the claim request 202 (e.g., by NDC number, drug/product name, etc.). It will be appreciated that the database 194 may be a local database, a networked database, or a remote database. The database 194 may be owned and/or updated by the enrollment computer 108, the service provider computer 104, the enrollment & validation module 105, or yet another entity (e.g., a data management service). In addition, block 320 may also verify that the enrollment or registration for the patient is still valid. For example, a matching record in the database 202 may further specify whether the enrolled or registered patient has obtained counseling or received/provided other information within a certain time period such that the enrollment or registration can be considered current. It will be appreciated that instead of directly accessing the database 202, the enrollment & validation module 105 can also submit a verification request with patient information (e.g., Cardholder ID, First Name/Last Name/DOB, etc.) to the enrollment computer 108, which can respond with an indication of whether the patient is enrolled or registered for one or more required healthcare programs for the prescribed product.

If block 320 determines that the patient is enrolled or registered for one or more required healthcare programs, then processing may proceed to block 335. At block 335, the enrollment & validation module 105 may determine whether additional processing or validation criteria (in addition to the patient enrollment validation at block 320) has been satisfied. As an example, additional processing or validation criteria in accordance with a REMS may include one or more of the following:

Validating that the Physician/Prescriber/Pharmacist identified by the claim request 202 (e.g., by Physician/Prescriber/Pharmacist Identifier) is registered, enrolled, or certified to dispense or provide the drug or product identified by the claim request 202 (e.g., by NDC identifier); and Validating that the Pharmacy identified by the claim request 202 (e.g., by Pharmacy Identifier) is registered, enrolled, or certified to dispense or provide the drug or product identified by the claim request 202 (e.g., by NDC or Service ID).

The foregoing example validation of block 335 may occur by the enrollment & validation module 105 determining whether the Physician/Prescriber/Pharmacist and/or Pharmacy identified in the claim request 202 is likewise identified by the database 194, or enrollment computer 108, as being registered, enrolled, or certified to handle the drug or product identified by the claim request 202 (e.g., by NDC or Service ID). Likewise, block 320 may also verify that the registrations, enrollments, or certifications for the physician/prescriber, pharmacy, and/or patient/caregiver are valid and have not expired.

It will be appreciated that the additional processing or validation criteria at block 335 may in accordance with REMS rules, according to an example embodiment of the invention. Alternatively, the additional processing or validation criteria at block 335 may be specified by billing compliance requirements of a claims processor (e.g., insurance company, pharmacy benefits manager (PBM), government payor, etc.). In addition or in the alternative, the additional processing or validation criteria may further be specified by other entities, including pharmaceutical manufacturers (e.g., in accordance with medication guides), governmental agencies (e.g., FDA), or other entities. Many variations of the example processing or validation criteria in block 335 will be available without departing from example embodiments of the invention. Likewise, other processing or validation criteria at block 335 may be associated with other types of checks and edits (e.g., validation based upon manufacturer or safety specifications associated with patient age, pregnancy status, quantity dispensed for the prescribed drug or product, days supply for the prescribed drug or product, dosage, or quantity dispensed/days supply ratio for the prescribed drug or product) without departing from example embodiments of the invention.

If the criteria in both blocks 320 and 335 are satisfied, then the enrollment & validation module 105 may provide a response 206 in the form of an approval response to the service provider computer 104. Based upon the approval response, at block 340, the service provider computer 104 may provide or otherwise deliver a copy of the claim request 202 as a claim request 208 to the claims processor computer 106 for benefits determination or other adjudication by an insurance company, PBM, government payor, discount program, or other payor. The claims processor computer 106 may then provide an adjudicated claim response 210 to the service provider computer 104. The adjudicated claim response 210 may indicate whether financial coverage for the claim request 208 was approved or denied. If approved, the adjudicated claim response 210 may include financial coverage information, including the covered amount and the patient pay amount (e.g., co-pay amount, co-insurance amount, etc.). Otherwise, if denied, the adjudicated claim response 210 may indicate one or more reasons for the denial of coverage. At block 345, the service provider computer 104 may then route or otherwise communicate a copy of the adjudicated claim response 210 as a claim response 212 to the pharmacy computer 102. The pharmacist may then fill, dispense, release, or otherwise provide the requested drug or product to the patient.

Figure 4:
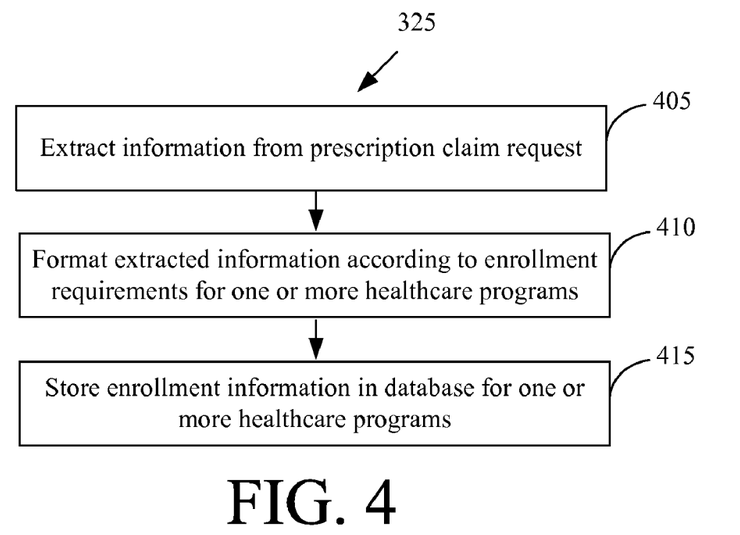
FIG. 4 illustrates an example flow diagram for facilitating an enrollment process, according to an example embodiment of the invention.

On the other hand, block 320 may determine that a patient has not registered or enrolled in one or more required healthcare programs, and processing may proceed to block 325. At block 325, the enrollment & validation module 105 may facilitate an enrollment process to enroll the patient in one or more required healthcare programs. An example process for block 325 will be discussed with reference to FIG. 4. Turning now to FIG. 4, at block 405, the enrollment & validation module 105 may extract patient enrollment information for the patient from the prescription claim request 202 received as part of the request 204. The extracted patient enrollment information can include one or more of the following information:

Patient Name
  i. Patient First Name
  ii. Patient Last Name
Cardholder ID and/or other identifier (e.g., person code)
Patient Date of Birth
Patient Age
Patient Gender
Patient Address (e.g., Street Address, Zip Code, etc.)
Patient Contact Information (e.g., Patient Telephone Number, email address, etc.)
Drug or product information (e.g., National Drug Code (NDC))
Diagnosis/Condition of Patient It will be appreciated that the extracted patient enrollment information illustrated herein is provided for example purposes only, and that other or alternative enrollment information can be extracted from a prescription claim request without departing from example embodiments of the invention. Moreover, in an alternative embodiment, in addition to extracting enrollment information from a prescription claim 204, the enrollment & validation module 105 can also extract additional enrollment information if needed or desired by communicating with a third-party entity or data source holding or storing healthcare information related to the patient. For example, initial enrollment information such as a first name/last name/date of birth, or Cardholder ID, from the prescription claim request can be used to obtain additional enrollment information from a third-party entity or data source that is associated with a healthcare data aggregator (e.g., WebMD, an eligibility verification entity, etc.), an insurance company or other third-party payor, a healthcare program provider, and the like.

Following block 405 is block 410. At block 410, the extracted patient enrollment information can be formatted according to one or more enrollment requirements for one or more healthcare programs. For example, the extracted enrollment information can be converted to fit within standardized fields required for enrollment in one or more healthcare programs. Following block 410 is block 415. At block 415, the extracted enrollment information, as formatted by block 410, may be stored by the enrollment & validation module 105 in enrollment database 194, either directly or indirectly by communicating with enrollment computer 105. It will be appreciated that the storage of the extracted enrollment information in database 194 may complete the enrollment of a patient for one or more healthcare programs, according to an example embodiment of the invention. Indeed, the extracted enrollment information may have included all of the required information to complete the patient enrollment in one or more healthcare programs. In this embodiment, a separate patient identifier may optionally be provided or assigned to the patient to designate the completed patient enrollment in one or more healthcare programs.

However, in another example embodiment, the storage of the extracted enrollment information in database 194 may represent only a partial or unfinished enrollment of the patient in one or more healthcare programs. In this embodiment, an individual such as a pharmacist or patient may need to interact with the enrollment computer 108, perhaps via a network or Internet website or portal to confirm the stored enrollment information and/or provide additional patient enrollment information to complete the enrollment process for one or more healthcare programs. The completion of block 415 in FIG. 4 may likewise correspond to a completion of block 325 in FIG. 2, although additional processing may be performed without departing from example embodiments of the invention.

Following block 325 is block 330. At block 330, the enrollment & validation module 105 can determine whether the performed enrollment process in block 325 was sufficient or otherwise completed the patient enrollment in one or more healthcare programs. If the prior enrollment process at block 320 was sufficient or completed the patient enrollment in one or more programs, then the enrollment & validation module 105 may provide a response 206 in the form of an approval response to the service provider computer 104, and processing may proceed to block 335 discussed earlier. If any other requirements or criteria of block 335, are satisfied, then at block 340, the service provider computer 104 may provide or otherwise deliver a copy of the claim request 202 to the claims processor computer 106 as a claim request 208 for benefits determination or other adjudication by an insurance company, PBM, government payor, discount program, or other payor. The claims processor computer 106 may then provide an adjudicated claim response 210 to the service provider computer 104, which can be communicated to the pharmacy computer 102 as a response 212 at block 345.

On the other hand, block 330 may determine that the patient enrollment in one or more programs is insufficient or incomplete. In this case, the enrollment & validation module 105 may provide a response 206 in the form of a denial response to the service provider computer 104, and processing may proceed to block 350. At block 350, the service provider computer 104 may halt further processing or adjudication of the prescription claim request 202. For example, at block 350, the service provider computer 104 may then provide the denial response to the pharmacy computer 102 as part of the claim response 212. Examples of denial responses, may include, but are not limited to, the following messages:

"Patient is not enrolled in [Healthcare Program Name]. Please visit [healthcare program Internet/website address] to complete the patient enrollment, and resubmit prescription claim for [Drug or Product Name]";

"Patient enrollment is not complete for [Healthcare Program Name]. Please visit [healthcare program Internet/website address] to complete the patient enrollment, and resubmit prescription claim for [Drug or Product Name]"; or Patient has not met the REMS requirement for the [Drug or Product Name]. Please visit [healthcare program Internet/website address] to review and complete the REMS requirement, and resubmit prescription claim for [Drug or Product Name]".

The pharmacy/pharmacist can then take corrective action as necessary based upon the denial response. For example, for patient enrollment in one or more required healthcare programs, the pharmacy/pharmacist can help a patient complete the patient enrollment process by visiting one or more network or Internet websites, which may be specified by the response 212, as will be described in further detail with respect to FIG. 5. Alternatively, the patient or a caregiver may visit one or more network or Internet websites to complete the patient enrollment process for one or more healthcare programs.

Upon completing the enrollment process, one or more records in the database 194 may be updated to reflect the patient enrollment in one or more healthcare programs. Optionally, a unique patient program identifier can be provided upon completion of the patient enrollment in some example embodiments of the invention. Accordingly, when the pharmacy computer 104 resubmits a prescription claim request 202 (which can optionally include the unique patient program identifier) at block 305, processing may proceed through blocks 310, 315, and 320, where the patient may be determined to have enrolled in one or more required healthcare programs. Accordingly, processing may proceed from block 320 to block 335, and assuming that all other requirements have been satisfied, blocks 340, 345 may be reached such that the prescription claim request 202 may be delivered as request 208 for adjudication by the claims processor computer 106. The service provider computer 104 can then receive an adjudication response 210 from claims processor computer 106, and the response 210 can be communicated to the pharmacy computer 102 as a response 212, according to an example embodiment of the invention.

It will also be appreciated that the service provider computer 104 and/or enrollment & validation module 105 may store reporting information, perhaps in the database 194. According to an example embodiment of the invention, the reporting information may include logs of claim statuses (e.g., approved and/or denied prescription claims); any patient enrollments that were facilitated along with their resulting statuses (e.g., completed enrollment, incomplete enrollment); the requested drug, product, or service; the reason(s) for any denials; and/or date/time information. The use of the logs may allow for further analysis of compliance with a REMS, billing guidelines, and/or other compliance programs.

Figure 2B:
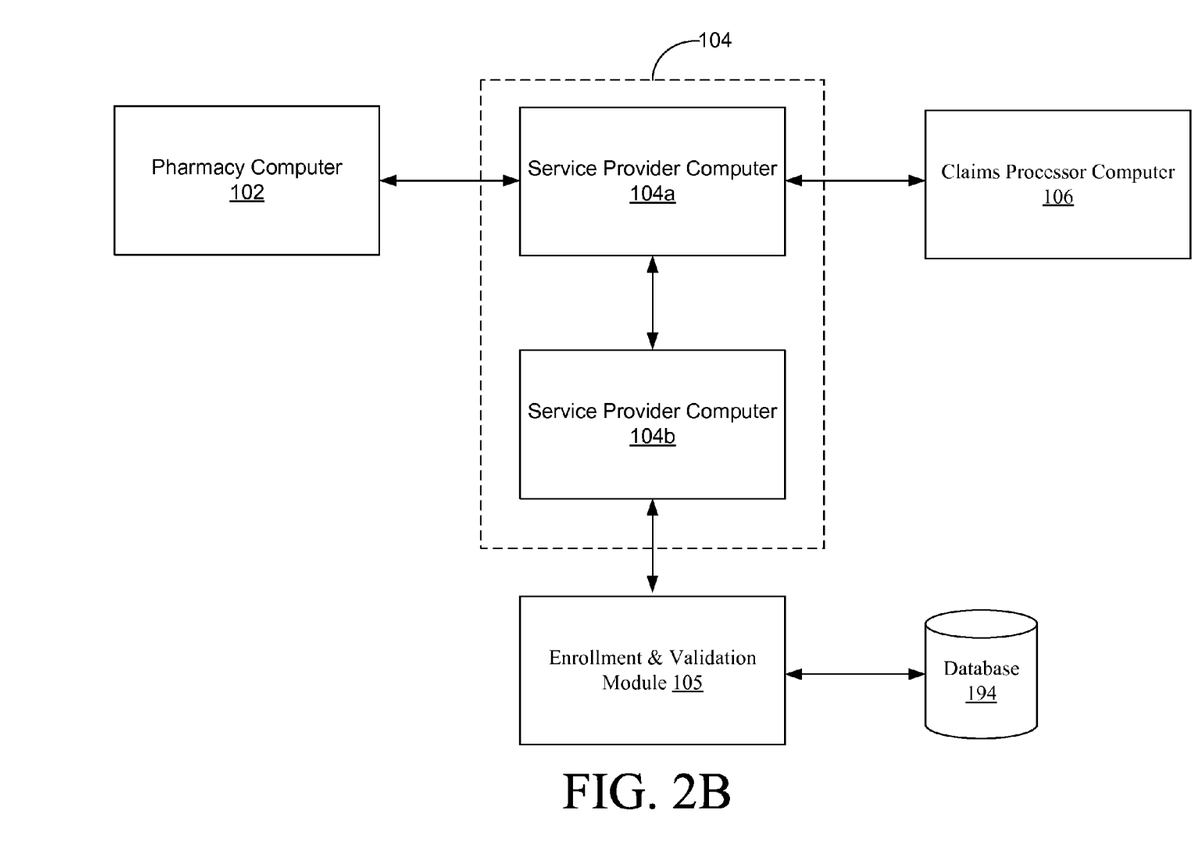
FIG. 2B illustrates a variation of the block diagram of FIG. 2A, according to an example embodiment of the invention.

It will be appreciated that many variations of FIGS. 2A and 3 are available without departing from example embodiments of the invention. For example, FIG. 2B illustrates a variation of the block diagrams of FIG. 2A, according to an example embodiment of the invention. As shown by FIG. 2B, the service provider computer 104 may be comprised of two or more distinct service providers 104a and 104b that are in communication with each other. Service provider computer 104a may be operative with the pharmacy computer 102 and claims processor computer while service provider computer 104b may be operative with other pharmacy computers and/or third-party processing computers. However, service provider computer 104b may have a data processing arrangement with service provider computer 104a. Under the data processing agreement, the service provider computer 104a may be permitted to utilize or offer services accessible via the service provider computer 104b, including the services of the enrollment & validation module 105. Accordingly, the services accessible via the service provider computer 104b, including the services of the enrollment & validation module 105, may be available to the pharmacy computer 102 via the service providers 104a and 104b.

Figure 5:
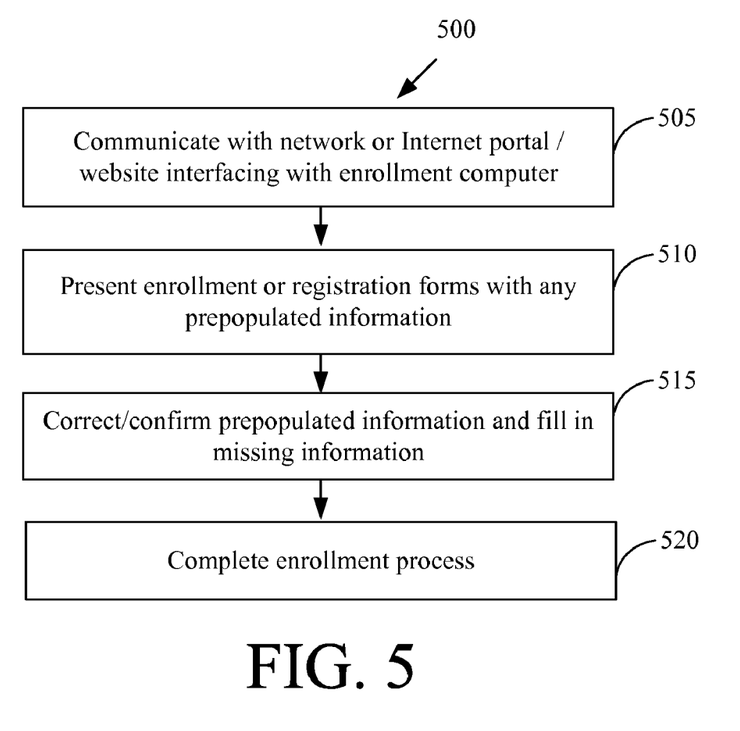
FIG. 5 illustrates a flow diagram of an example process for completing a patient enrollment for one or more healthcare programs, according to an example embodiment of the invention.

FIG. 5 illustrates a flow diagram 500 of an example process for completing a patient enrollment for one or more healthcare programs, according to an example embodiment of the invention. Turning to FIG. 5, at block 505, a pharmacist or patient may utilize a computer (e.g., a pharmacy computer 102 or another computer such as a home or personal computer) to access one or more websites supporting patient enrollment for one or more healthcare programs. The one or more websites can be operated by the enrollment computer 108 or a web server in communication with or otherwise affiliated with the enrollment computer 108.

At block 510, the one or more websites may present one or more web pages having one or more enrollment/registration forms for one or more healthcare programs. The one or more enrollment/registration forms can display prepopulated information, which may comprise the extracted patient enrollment information previously stored in database 194 in accordance with block 325 of FIG. 3. The availability of the prepopulated information can facilitate or otherwise shorten the process or completing the patient enrollment for one or more healthcare programs.

At block 515, the pharmacist or patient can verify that the prepopulated information provided for the one or more enrollment/registration forms. The pharmacist or patient can modify any portion of the prepopulated information that is incomplete or incorrect, according to an example embodiment of the invention. The pharmacist or patient can also fill in any missing information, if required or desired, in the one or more enrollment/registration forms. The missing information may not have been available from the extracted patient enrollment information that was utilized for prepopulation. The missing information that is received from the pharmacist or patient can include one or more of the following: patient medical history, other drugs being utilized by patient, patient conditions. In addition, the missing information can also include licensure information for a patient or provider licensed or trained to utilize, handle, or prescribe a particular product.

At block 520, once the prepopulated information has been verified/corrected and any required missing enrollment information is received, then the enrollment process may be completed, and the appropriate records in database 194 may be updated, perhaps by the website operating in conjunction with the enrollment computer 102. In an example embodiment of the invention, the completion of the patient enrollment process may result in a unique patient program identifier being provided. The patient program identifier may be utilized by the pharmacy for any subsequently transmitted prescription claim requests so that the appropriate records in database 194 can be retrieved for determining that the patient has enrolled in one or more healthcare programs.

It will be appreciated that while the above enrollment process was discussed with respect to an Internet portal/website, the enrollment computer 102 can also support enrollments via a call center 208, an interactive voice response system 209, and the like without departing from example embodiments of the invention.

The invention is described above with reference to block and flow diagrams of systems, methods, apparatuses, and/or computer program products according to example embodiments of the invention. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments of the invention.

These computer-executable program instructions may be loaded onto a general purpose computer, a special-purpose computer, a processor, or other programmable data processing apparatus to produce a particular machine, such that the instructions that execute on the computer, processor, or other programmable data processing apparatus create means for implementing one or more functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments of the invention may provide for a computer program product, comprising a computer usable medium having a computer readable program code or program instructions embodied therein, said computer readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special purpose hardware and computer instructions.

It will be appreciated that each of the memories and data storage devices described herein can store data and information for subsequent retrieval. The memories and databases can be in communication with each other and/or other databases, such as a centralized database, or other types of data storage devices. When needed, data or information stored in a memory or database may be transmitted to a centralized database capable of receiving data, information, or data records from more than one database or other data storage devices. In other embodiments, the databases shown can be integrated or distributed into any number of databases or other data storage devices.

It will also be appreciated that each of the I/O interfaces described herein may facilitate communication between a processor and various I/O devices, such as a keyboard, mouse, printer, microphone, speaker, monitor, bar code readers/scanners, RFID readers, and the like. Likewise, each of the network interfaces described herein may take any of a number of forms, such as a network interface card, a modem, a wireless network card, and the like.

It will further be appreciated that while certain computers have been illustrated herein as a single computer or processor, the illustrated computers may actually be comprised of a group of computers or processors, according to an example embodiment of the invention.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method, comprising:
   receiving a prescription claim request from a pharmacy computer, wherein the prescription claim request includes at least (i) a first product identifier identifying a prescribed product for a patient, and (ii) patient information associated with the patient;
   automatically determining, based at least in part upon the first product identifier, that the patient is subject to a requirement to enroll in one or more required healthcare programs based on the prescription product as part of a Risk Evaluation and Mitigation Strategy (REMS) prior to the prescription product being released to the patient;
   automatically extracting enrollment information from the prescription claim request, the extracted enrollment information including at least a portion of the patient information from the prescription claim request; and
   automatically utilizing the extracted enrollment information to complete at least a portion of an enrollment process for the one or more required healthcare programs, wherein the prior steps are performed by one or more computers associated with a service provider.

2. The method of claim 1, wherein the one or more required healthcare programs includes at least one medication therapy management (MTM) program for the prescribed product, or at least one Disease/Condition Management service.

3. The method of claim 1, wherein prior to extracting the enrollment information from the prescription claim request, the method further comprises:
   determining that the patient is not currently enrolled in the one or more required healthcare programs,
   wherein the prior step is performed by one or more computers associated with the service provider.

4. The method of claim 3, wherein the extracted enrollment information is utilized to complete all of the enrollment process for the one or more required healthcare programs, and further comprising:
   responsive to the completion of all of the enrollment process, facilitating adjudication of the prescription claim request with at least one claims processor computer; and
   delivering a response to the pharmacy computer with a result of the adjudication of the prescription claim request,
   wherein the prior steps are performed by one or more computers associated with the service provider.

5. The method of claim 3, wherein the extracted enrollment information is utilized to complete only a portion of the enrollment process for the one or more required healthcare programs, and further comprising:
   responsive to completing only the portion of the enrollment process, delivering a rejection response for the prescription claim request to the pharmacy computer,
   wherein the prior step is performed by one or more computers associated with the service provider.

6. The method of claim 5, wherein the rejection response requests completion of the enrollment process for the one or more required healthcare programs.

7. The method of claim 5, wherein the enrollment process is completed by receiving additional patient information via one or more websites, wherein the one or more websites request at least one of (i) additional information not available from the extracted enrollment information, or (ii) confirmation of accuracy of the extracted enrollment information.

8. The method of claim 7, wherein the one or more websites requests confirmation of accuracy of the extracted enrollment information, wherein the one or more websites automatically populate one or more web pages with the extracted enrollment information for confirmation.

9. The method of claim 5, wherein the rejection response identifies one or more websites to access in order to complete the enrollment process for the one or more required healthcare programs.

10. The method of claim 1, wherein the extracted enrollment information includes one or more of (i) a patient name, (ii) a patient date of birth, (iii) a patient address, (iii) patient telephone number, or (iv) a patient condition.

11. A system, comprising:
    at least one memory for storing computer-executable instructions; and
    at least one processor in communication with the at least one memory, wherein the at least one processor is configured to execute the computer-executable instructions to:
    receive a prescription claim request from a pharmacy computer, wherein the prescription claim request includes at least (i) a first product identifier identifying a prescribed product for a patient, and (ii) patient information associated with the patient;
    determine automatically, based at least in part upon the first product identifier, that the patient is subject to a requirement to enroll in one or more required healthcare programs based on the prescription product as part of a Risk Evaluation and Mitigation Strategy (REMS) prior to the prescription product being released to the patient;
    extract enrollment information automatically from the prescription claim request, the extracted enrollment information including at least a portion of the patient information from the prescription claim request; and automatically utilize the extracted enrollment information to complete at least a portion of an enrollment process for the one or more required healthcare programs.

12. The system of claim 11, wherein the one or more required healthcare programs includes at least one medication therapy management (MTM) program for the prescribed product, or at least one Disease/Condition Management service.

13. The system of claim 11, wherein prior to extracting the enrollment information from the prescription claim request, the at least one processor is further configured to execute the computer-executable instructions to:

determine that the patient is not currently enrolled in the one or more required healthcare programs.

14. The system of claim 13, wherein the extracted enrollment information is utilized to complete all of the enrollment process for the one or more required healthcare programs, and wherein the at least one processor is further configured to execute the computer-executable instructions to:

responsive to the completion of all of the enrollment process, facilitate adjudication of the prescription claim request with at least one claims processor computer; and deliver a response to the pharmacy computer with a result of the adjudication of the prescription claim request.

15. The system of claim 13, wherein the extracted enrollment information is utilized to complete only a portion of the enrollment process for the one or more required healthcare programs, and wherein the at least one processor is further configured to execute the computer-executable instructions to:

responsive to completing only the portion of the enrollment process, deliver a rejection response for the prescription claim request to the pharmacy computer.

16. The system of claim 15, wherein the rejection response requests completion of the enrollment process for the one or more required healthcare programs.

17. The system of claim 15, wherein the enrollment process is completed by receiving additional patient information via one or more websites, wherein the one or more websites request at least one of (i) additional information not available from the extracted enrollment information, or (ii) confirmation of accuracy of the extracted enrollment information.

18. The system of claim 17, wherein the one or more websites requests confirmation of accuracy of the extracted enrollment information, wherein the one or more websites automatically populate one or more web pages with the extracted enrollment information for confirmation.

19. The system of claim 15, wherein the rejection response identifies one or more websites to access in order to complete the enrollment process for the one or more required healthcare programs.

20. The system of claim 11, wherein the extracted enrollment information includes one or more of (i) a patient name, (ii) a patient date of birth, (iii) a patient address, (iii) patient telephone number, or (iv) a patient condition.

* * * * *